(12) United States Patent
Okuno

(10) Patent No.: US 8,248,889 B2
(45) Date of Patent: Aug. 21, 2012

(54) ULTRASOUND DIAGNOSTIC APPARATUS

(75) Inventor: Yoshiyuki Okuno, Fussa (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/218,630

(22) Filed: Aug. 26, 2011

(65) Prior Publication Data

US 2012/0069715 A1    Mar. 22, 2012

Related U.S. Application Data

(63) Continuation of application No. PCT/JP2011/059080, filed on Apr. 12, 2011.

(30) Foreign Application Priority Data

Apr. 12, 2010  (JP) ................... 2010-091672

(51) Int. Cl.
*A61B 8/00* (2006.01)
(52) U.S. Cl. ....................... 367/181; 367/180
(58) Field of Classification Search ................ 367/180, 367/138, 181; 600/437
See application file for complete search history.

(56) References Cited

U.S. PATENT DOCUMENTS

| | | | |
|---|---|---|---|
| 2008/0064959 A1* | 3/2008 | Kanda et al. ................ | 600/459 |
| 2010/0036257 A1 | 2/2010 | Sano et al. | |
| 2012/0069715 A1* | 3/2012 | Okuno ....................... | 367/180 |

FOREIGN PATENT DOCUMENTS

| | | |
|---|---|---|
| JP | 2006-319713 | 11/2006 |
| JP | 2007-029259 | 2/2007 |
| JP | 2008-136725 | 6/2008 |
| JP | 2009-279033 | 12/2009 |
| WO | WO 2005/120130 A1 | 12/2005 |
| WO | WO 2011129326 A1 * | 10/2011 |

OTHER PUBLICATIONS

European Search Report dated Mar. 1, 2012 from corresponding European Patent Application No. EP 11 76 8847.3.

* cited by examiner

*Primary Examiner* — Daniel Pihulic
(74) *Attorney, Agent, or Firm* — Scully, Scott, Murphy & Presser, P.C.

(57) ABSTRACT

An ultrasound diagnostic apparatus is connectable with an ultrasound probe having a c-MUT element or a piezoelectric ultrasound transducer, and includes a DC bias output portion, a transmission signal output portion, an operation portion, a control portion, and a display portion. The control portion controls the DC bias output portion and the transmission signal output portion so as to output an ultrasound transmission signal after applying the bias voltage when an instruction signal instructing the start of transmission is inputted from the operation portion, and so as to stop application of the bias voltage after stopping output of the ultrasound transmission signal when an instruction signal that instructs stopping of transmission is inputted from the operation portion. The control portion causes a connection state showing which one of the c-MUT element and the capacitive micro-machined ultrasonic transducer is connected to be displayed on the display portion.

6 Claims, 7 Drawing Sheets

ULTRASOUND DIAGNOSTIC APPARATUS

CROSS REFERENCE TO RELATED APPLICATION

This application is a continuation application of PCT/JP2011/059080 filed on Apr. 12, 2011 and claims benefit of Japanese Application No. 2010-091672 filed in Japan on Apr. 12, 2010, the entire contents of which are incorporated herein by this reference.

BACKGROUND OF THE INVENTION

1. Field of the Invention

The present invention relates to an ultrasound diagnostic apparatus to which an ultrasound probe having a capacitive micro-machined ultrasonic transducer can be connected.

2. Description of the Related Art

Conventionally, a ceramic piezoelectric material PZT (lead zirconate titanate) has been used for piezoelectric elements that convert electrical signals into ultrasound in ultrasound transducers. However, a capacitive micro-machined ultrasonic transducer (hereunder, referred to as "c-MUT element") that is obtained by processing a silicon semiconductor substrate using silicon micro-machining technology is attracting attention.

A c-MUT element includes a planar first electrode that is provided on a silicon substrate, and a planar second electrode that is provided so as to face the first electrode with a predetermined cavity therebetween.

In an ultrasound diagnostic apparatus that generates an ultrasound diagnostic image using an ultrasound probe having the above described c-MUT element, transmission and reception of ultrasound is performed by applying a driving signal to one of the electrodes of the c-MUT element while applying a bias voltage between the two electrodes to thereby cause a film (a membrane constituting the second electrode) at an upper part of the cavity to vibrate and transmit ultrasound, and detecting a returned echo signal with the film at the upper part of the cavity.

That is, the c-MUT element requires not only a driving signal that is an RF signal for generating ultrasound, but also requires a bias voltage at both a time of transmission and reception. Consequently, the sensitivity of the c-MUT element can be controlled by changing the bias level applied thereto.

However, application of an excessive bias voltage to a c-MUT element causes a short circuit in the c-MUT element, and as a result an overcurrent state is entered which leads to damage of the c-MUT element.

To prevent such kind of damage to a c-MUT element due to application of an excessive bias voltage, technology has been proposed in which overvoltage detection means is provided between the electrodes on the c-MUT element side and a bias power source, and application of a bias voltage is stopped when application of an excessive bias voltage is detected by the overvoltage detection means (for example, see Japanese Patent Application Laid-Open Publication No. 2007-29259).

Further, when the size of a bias voltage applied between the electrodes of a c-MUT element exceeds a predetermined range, a drum-shaped sacrificial layer that is inserted between the electrodes enters a crushed state, i.e. a collapsed state. To prevent excessive output of ultrasound to a subject at the time of such a collapsed state, an ultrasound transducer and an ultrasound diagnostic apparatus have been proposed that have a protection circuit that is configured to detect a DC bias voltage, and if the detected DC bias voltage exceeds a threshold value, to cut off an electrical connection between a DC bias circuit and the ultrasound transducer by means of a switch (for example, see Japanese Patent Application Laid-Open Publication No. 2008-136725).

Furthermore, other examples of the prior art include, for example, as disclosed in International Publication No. WO 2005/120130, an ultrasound probe apparatus that, at a time of transmission, superimposes an RF signal, that is, a driving signal, on a DC bias voltage that is outputted from a DC bias generation circuit to an ultrasound transducer of a detachable ultrasound probe.

SUMMARY OF THE INVENTION

An ultrasound diagnostic apparatus according to one aspect of the present invention is connectable with an ultrasound probe having a capacitive micro-machined ultrasonic transducer whose sensitivity can be controlled in accordance with an applied bias voltage, and includes: a bias voltage output portion capable of varying the bias voltage that is applied to the capacitive micro-machined ultrasonic transducer; a transmission signal output portion that outputs an ultrasound transmission signal to the capacitive micro-machined ultrasonic transducer; an operation portion that outputs an instruction signal that instructs the ultrasound diagnostic apparatus including the bias voltage output portion and the transmission signal output portion; and a control portion that, based on an instruction signal from the operation portion, controls the bias voltage output portion and the transmission signal output portion to control output timings of the bias voltage and the transmission signal so as to output the ultrasound signal after outputting the bias voltage or to stop output of the bias voltage after stopping output of the ultrasound signal; wherein: a piezoelectric ultrasound transducer that does not require bias voltage control can be connected to the ultrasound diagnostic apparatus, and the ultrasound diagnostic apparatus further includes a display portion that displays an ultrasound image based on a reception signal that is received by the capacitive micro-machined ultrasonic transducer; and the control portion causes a connection state that shows which one of the piezoelectric ultrasound transducer and the capacitive micro-machined ultrasonic transducer is connected to be displayed on the display portion.

DETAILED DESCRIPTION OF THE PREFERRED EMBODIMENTS

Figure 1:
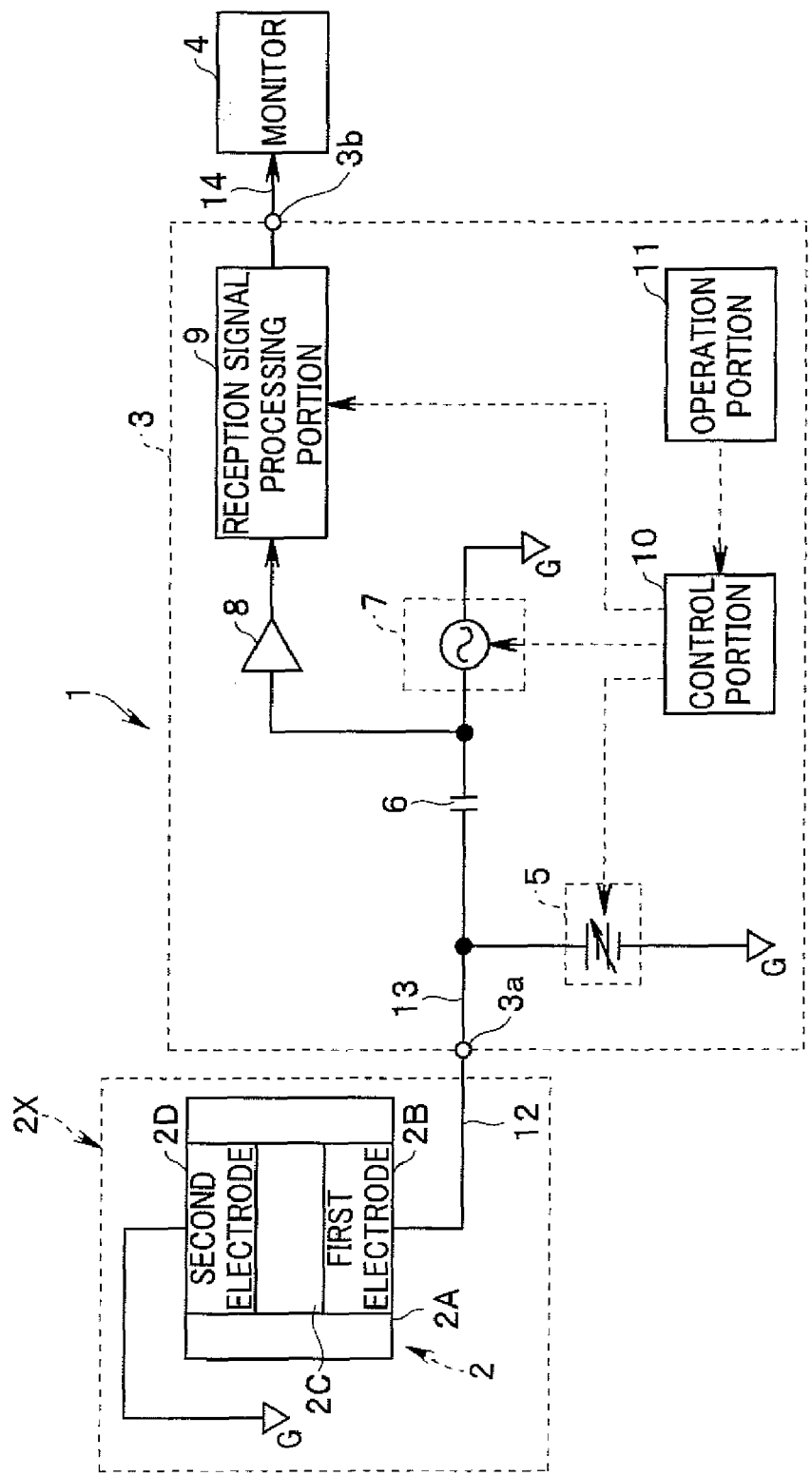
FIG. 1 is a block diagram that shows the overall configuration of an ultrasound diagnostic apparatus according to a first embodiment of the present invention.

Embodiments of the present invention are described in detail hereunder while referring to the drawings.

First Embodiment

FIG. 1 to FIG. 4 relate to a first embodiment of the present invention. FIG. 1 is a block diagram that shows the overall configuration of an ultrasound diagnostic apparatus according to the present embodiment.

An ultrasound diagnostic apparatus 1 according to the present embodiment that is shown in FIG. 1 includes: an ultrasound probe 2X that has a capacitive micro-machined ultrasonic transducer (c-MUT element) 2; an ultrasound observation apparatus 3 to which the ultrasound probe 2X is connectable, and which drives the c-MUT element 2 and performs processing to receive an echo signal obtained by the c-MUT element 2; and a monitor 4 that, by receiving input of ultrasound image data that is outputted from the ultrasound observation apparatus 3, displays an ultrasound image of a subject that has been scanned with an ultrasound beam by means of the c-MUT element 2.

The c-MUT element 2 of the ultrasound probe 2X includes a planar first electrode 2B that is provided on a silicon substrate 2A, and a planar second electrode 2D that is provided so as to face the first electrode 2B with a predetermined cavity 2C therebetween. In this connection, although not shown in the drawings, the second electrode 2D includes a membrane for transmitting ultrasound and for detecting an echo signal.

According to the configuration shown in FIG. 1, a DC bias voltage (hereunder, referred to simply as "bias voltage") and a transmission signal as a driving signal that is an RF signal are applied to the first electrode 2B of the c-MUT element 2 from the ultrasound observation apparatus 3.

That is, the first electrode 2B is connected to a connection terminal 3a of the ultrasound observation apparatus 3 by a signal wire 12. The second electrode 2D is grounded. Note that, although not shown in the drawings, at least the c-MUT element 2 and the signal wire 12 are provided inside an insertion portion having a bending portion and a flexible tube portion of the ultrasound probe 2X.

The ultrasound observation apparatus 3 includes the connection terminal 3a, a DC bias output portion 5, a bias component cut-off capacitor 6, a transmission signal output portion 7, a reception signal amplifier 8, a reception signal processing portion 9, a control portion 10, and an operation portion 11.

Inside the ultrasound observation apparatus 3, the connection terminal 3a is connected to the DC bias output portion 5 through a signal wire 13 and is connected to the transmission signal output portion 7 through the bias component cut-off capacitor 6.

The DC bias output portion 5 generates a bias voltage that is required to drive the c-MUT element 2, and outputs the generated bias voltage to the first electrode 2B of the c-MUT element 2 via the signal wire 13, the connection terminal 3a, and the signal wire 12. The DC bias output portion 5 is configured to be capable of varying the bias voltage applied to the c-MUT element 2. Note that the other end of the DC bias output portion 5 is grounded.

Further, the transmission signal output portion 7 generates an RF signal, that is, a transmission signal that is a driving signal, that is required to drive the c-MUT element 2, and outputs the generated transmission signal to the first electrode 2B of the c-MUT element 2 via the signal wire 13, the connection terminal 3a, and the signal wire 12. Note that the other end of the transmission signal output portion 7 is grounded.

Thus, according to the configuration shown in FIG. 1, a bias voltage and a transmission signal are applied to the first electrode 2B of the c-MUT element 2, and in this case, the bias voltage is applied in a manner in which the bias voltage is superimposed on the transmission signal.

Further, a mid-point of the signal wire 13 between the bias component cut-off capacitor 6 and the transmission signal output portion 7 is connected to the reception signal processing portion 9 via the reception signal amplifier 8 by the signal wire 13.

The bias component cut-off capacitor 6 is provided between the DC bias output portion 5 and the transmission signal output portion 7. The bias component cut-off capacitor 6 prevents a DC component of the bias voltage from entering a transmission and reception circuit system that includes the transmission signal output portion 7 and the reception signal processing portion 9.

A reception signal (echo signal) that is obtained by driving the c-MUT element 2 by application of the bias voltage and the transmission signal passes through the bias component cut-off capacitor 6 and is amplified by the reception signal amplifier 8, and is thereafter inputted to the reception signal processing portion 9.

The reception signal processing portion 9 generates ultrasound image data by subjecting the inputted reception signal to signal processing, and outputs the generated ultrasound image data to the output terminal 3b. The monitor 4 is connected via the signal wire 14 to the output terminal 3b. The ultrasound image data that is outputted to the output terminal 3b is displayed by the monitor 4.

The operation portion 11 is connected to the control portion 10. The operation portion 11 has various operation keys including, for example, a freeze release key, a freeze key, and a transmission start/transmission stop key. An instruction signal that is an operation signal generated by operation of any of the various operation keys of the operation portion 11 is supplied by the operation portion 11. For example, the operation portion 11 outputs an instruction signal that instructs the release of a freeze state or the start of a freeze operation, an instruction signal that instructs the start of transmission, and an instruction signal that instructs stopping of transmission to the control portion 10.

The control portion 10 can control the DC bias output portion 5, the transmission signal output portion 7, and the reception signal processing portion 9 based on the supplied instruction signal. That is, the control portion 10 controls an output (transmission) timing of a bias voltage and a transmission signal that are applied to the c-MUT element 2, and a timing of processing a reception signal obtained by the c-MUT element 2.

Figure 2:
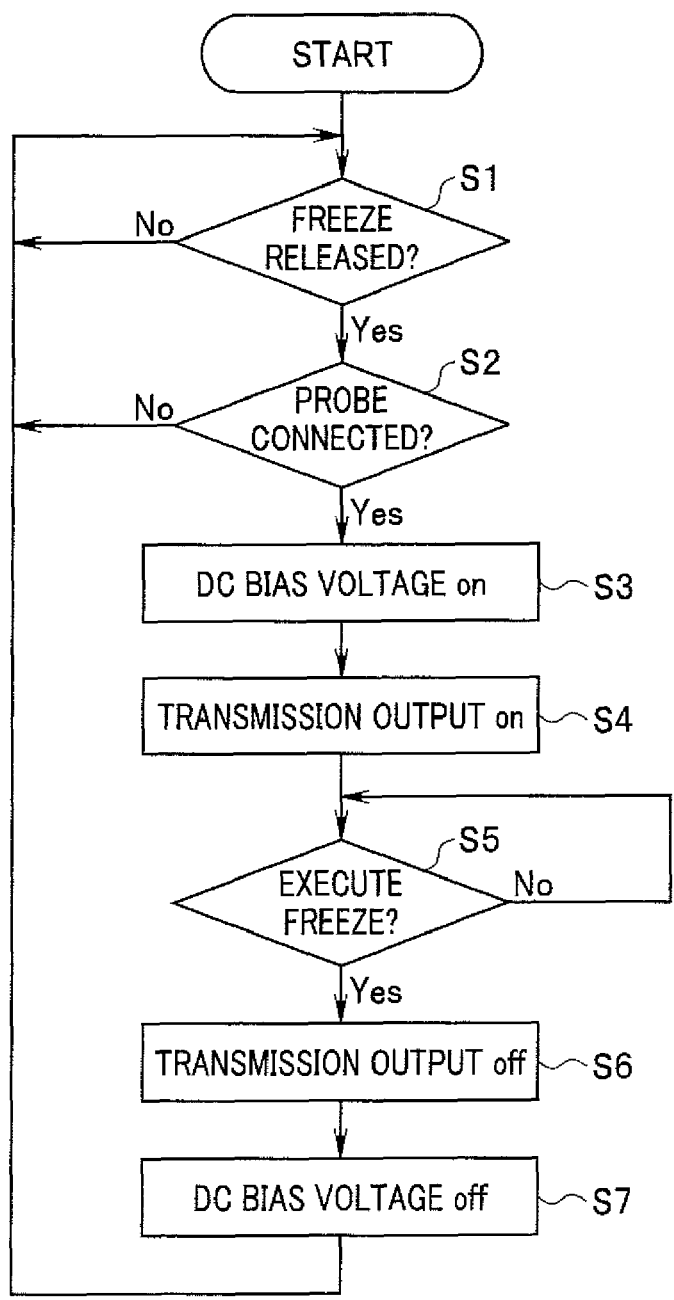
FIG. 2 is a flowchart that illustrates an example of control of a control portion shown in FIG. 1.
Figure 3:
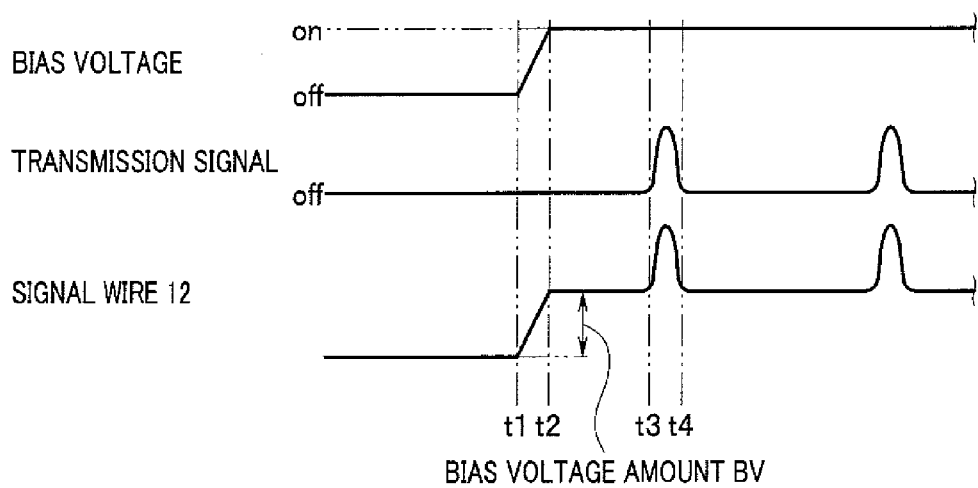
FIG. 3 is a time chart for describing operations of the ultrasound diagnostic apparatus according to the first embodiment.
Figure 4:
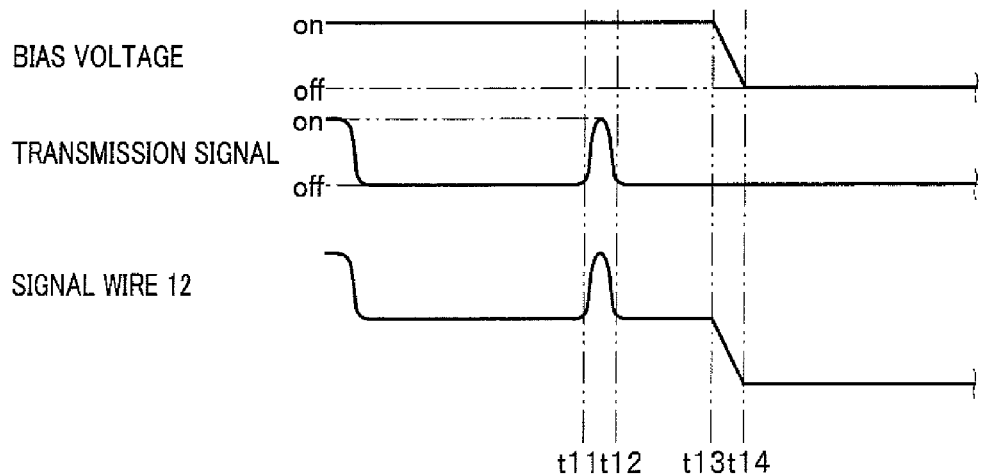
FIG. 4 is a time chart for describing operations of the ultrasound diagnostic apparatus according to the first embodiment.

Next, operations of the ultrasound diagnostic apparatus of the present embodiment are described using FIG. 2 to FIG. 4.

In the ultrasound diagnostic apparatus 1 of the present embodiment, when an instruction signal that instructs the start of transmission is inputted from the operation portion 11 to the control portion 10, the control portion 10 controls the DC bias output portion 5 and the transmission signal output portion 7 so as to output a bias voltage and thereafter output a transmission signal. Further, when an instruction signal that instructs stopping of transmission is inputted from the operation portion 11, the control portion 10 controls the DC bias output portion 5 and the transmission signal output portion 7 so as to stop output of the transmission signal and thereafter stop output of the bias voltage.

Further, the control portion 10 controls the DC bias output portion 5 so as not to apply the bias voltage when the power supply of the ultrasound diagnostic apparatus 1 is turned on.

A flowchart that illustrates a specific example of control of the control portion 10 from the time of activating the apparatus is shown in FIG. 2.

Here, it is assumed that the power supply is turned on by switching on an unshown power switch to carry out diagnosis and examination of a subject using the ultrasound diagnostic apparatus of the present embodiment.

After the power supply is turned on, the control portion 10 of the ultrasound diagnostic apparatus 1 reads out a program for performing the processing shown in FIG. 2 from an unshown memory and executes the program, and simultaneously controls so as to execute a freeze mode.

At this time, since the freeze mode is executed after the power supply is turned on, the ultrasound observation apparatus 3 enters a state in which a bias voltage from the DC bias output portion 5 is not supplied to the c-MUT element 2. That is, when the power supply of the ultrasound diagnostic apparatus 1 is turned on, the control portion 10 controls the DC bias output portion 5 so as not to apply a bias voltage to the c-MUT element 2.

Subsequently, when executing the program for performing the processing shown in FIG. 2, in the determination processing in step S1, based on an instruction signal supplied from the operation portion 11, the control portion 10 determines whether or not the freeze mode has been released by operation of the freeze release key of the operation portion 11 (alternatively, the freeze mode has been released by operation of the freeze key).

If an instruction to release the freeze mode has been inputted by an operation of the operation portion 11, next, in step S2, the control portion 10 confirms that the c-MUT element 2 is connected. Thereafter, in the processing in step S3, the control portion 10 controls the DC bias output portion 5 so as to output a bias voltage to the c-MUT element 2. Subsequently, in the processing in step S4, the control portion 10 controls the transmission signal output portion 7 so as to output a transmission signal.

In this connection, a determination as to whether or not the c-MUT element 2 is connected in the aforementioned step S2 is carried out, for example, by detecting an electrical current value that flows to the c-MUT element 2 and determining whether or not the c-MUT element 2 is connected based on the detection result. Alternatively, a configuration may be adopted that uses known technology that determines whether or not the c-MUT element 2 is connected by assembling the c-MUT element 2 in an ultrasound probe shape, providing a connector pin that connects with the apparatus in the probe, and determining whether or not the c-MUT element 2 is connected according to an open/short state of the pin.

Changes in the bias voltage and the transmission signal from the time that the power supply is turned on are illustrated in FIG. 3. Note that, a bias voltage shown in FIG. 3 represents a bias voltage that is an output of the DC bias output portion 5, a transmission signal shown in FIG. 3 represents a transmission signal that is an output of the transmission signal output portion 7, and a signal wire 12 shown in FIG. 3 represents a superimposed signal that is applied via the signal wire 12 connected to the c-MUT element 2.

As shown in FIG. 3, for example, when it is assumed that a freeze release operation is carried out at a time t1, at such time the DC bias output portion 5 is turned on by the control portion 10. Thereupon, as shown by the bias voltage in FIG. 3, the DC bias output portion 5 gradually increases a bias voltage value during a period from the time t1 to a time t2. The DC bias output portion 5 outputs the bias voltage so as to be a predetermined value that has been previously set at the time t2.

As shown by the signal wire 12 in FIG. 3, during the period from the time t1 to the time t2, a change in the level of a signal applied to the first electrode 2B of the c-MUT element 2 via the signal wire 12 that is connected thereto increases from a zero line to a bias voltage amount BV that has increased by a voltage amount that is the same as the amount of increase in the bias voltage (see the bias voltage in FIG. 3).

Thereafter, when outputting a transmission signal in the aforementioned step S4, as shown by the transmission signal in FIG. 3, the transmission signal output portion 7 outputs a transmission signal at a timing such that the transmission signal rises at a time t3 and falls at a time t4.

When the transmission signal is outputted at such a timing, as shown by the signal wire 12 in FIG. 3, a transmission signal is outputted to the signal wire 12 in a form in which the transmission signal is superimposed on the bias voltage amount BV during the period from the time t3 to the time t4.

Thereafter, when the transmission signal shown by the signal wire 12 in FIG. 3 is outputted to the c-MUT element 2 through the signal wire 12, the c-MUT element 2 generates ultrasound by means of the membrane of the second electrode 2D, detects a returned echo signal by means of the membrane of the second electrode 2D, and outputs the echo signal to the ultrasound observation apparatus 3. As a result, the inputted echo signal that is a reception signal is processed by the reception signal processing portion 9 of the ultrasound observation apparatus 3 and thereby converted into ultrasound image data. Thereafter, the ultrasound image data is displayed using the monitor 4.

Returning again to FIG. 2, while continuing output of the transmission signal in the processing in step S4 as described above, the control portion 10 carries out determination processing in the subsequent step S5. In the determination processing in step S5, based on an instruction signal supplied from the operation portion 11, the control portion 10 determines whether or not a request has been made to execute the freeze mode by operation of the freeze key of the operation portion 11.

If an instruction has been inputted to request execution of the freeze mode by operation of the operation portion 11, in the subsequent step S6, the control portion 10 controls the transmission signal output portion 7 so as to stop output of the transmission signal. Thereafter, in the processing in step S7, the control portion 10 controls the DC bias output portion 5 so as to stop output of the bias voltage that is being outputted to the c-MUT element 2.

Changes in the bias voltage and transmission signal from the time that the freeze mode is executed in this manner are shown in FIG. 4. Note that, a bias voltage shown in FIG. 4 represents a bias voltage that is an output of the DC bias output portion 5, a transmission signal shown in FIG. 4 represents a transmission signal that is an output of the transmission signal output portion 7, and a signal wire 12 shown in FIG. 4 represents a superimposed signal that is applied via the signal wire 12 that is connected to the c-MUT element 2.

As shown in FIG. 4, for example, when it is assumed that the freeze mode has been executed before a time t13, by the processing in the above described step S6, the transmission signal output portion 7 is controlled so as to stop output of the transmission signal that was being outputted. Thus, as shown by the transmission signal in FIG. 4, the transmission signal is not outputted from the time t13 onwards.

Thereafter, by the processing in step S7, the DC bias output portion 5 is turned off at the time t13. Thus, as shown by the bias voltage in FIG. 4, the DC bias output portion 5 gradually decreases the bias voltage amount BV during the period from the time t13 to a time t14, and stops (turns off) the output of the bias voltage so that the bias voltage is zero at the time t14.

As shown by the signal wire 12 in FIG. 4, during a period from the time t13 to the time t14, a change in the level of a signal applied to the first electrode 2B of the c-MUT element 2 via the signal wire 12 that is connected thereto is a signal change in which the transmission signal (see the transmission signal in FIG. 4) that had been superimposed on the bias voltage ceases, and then the bias voltage ceases in a manner in which the bias voltage amount BV that had been superimposed decreases and becomes zero.

The control portion 10 executes the freeze mode in this manner, and thereafter returns the processing to step S1 to continue the determination processing in step S1.

As described above, when the freeze mode is released, the control portion 10 applies a bias voltage and thereafter outputs a transmission signal. Subsequently, when the freeze mode is executed, by the opposite procedure to that when the freeze mode is released, the control portion 10 stops output of the transmission signal and thereafter stops output of the bias voltage. That is, these processing procedures performed by the control portion 10 can prevent a transmission signal being outputted in a state in which a DC bias voltage is not applied to the c-MUT element 2.

Thus, according to the present embodiment, since a bipolar transmission signal having positive and negative values is not transmitted to the c-MUT element 2 in a state in which a bias voltage is not being applied thereto, damage of the c-MUT element 2 can be prevented by simple control as described above.

Second Embodiment

Figure 5:
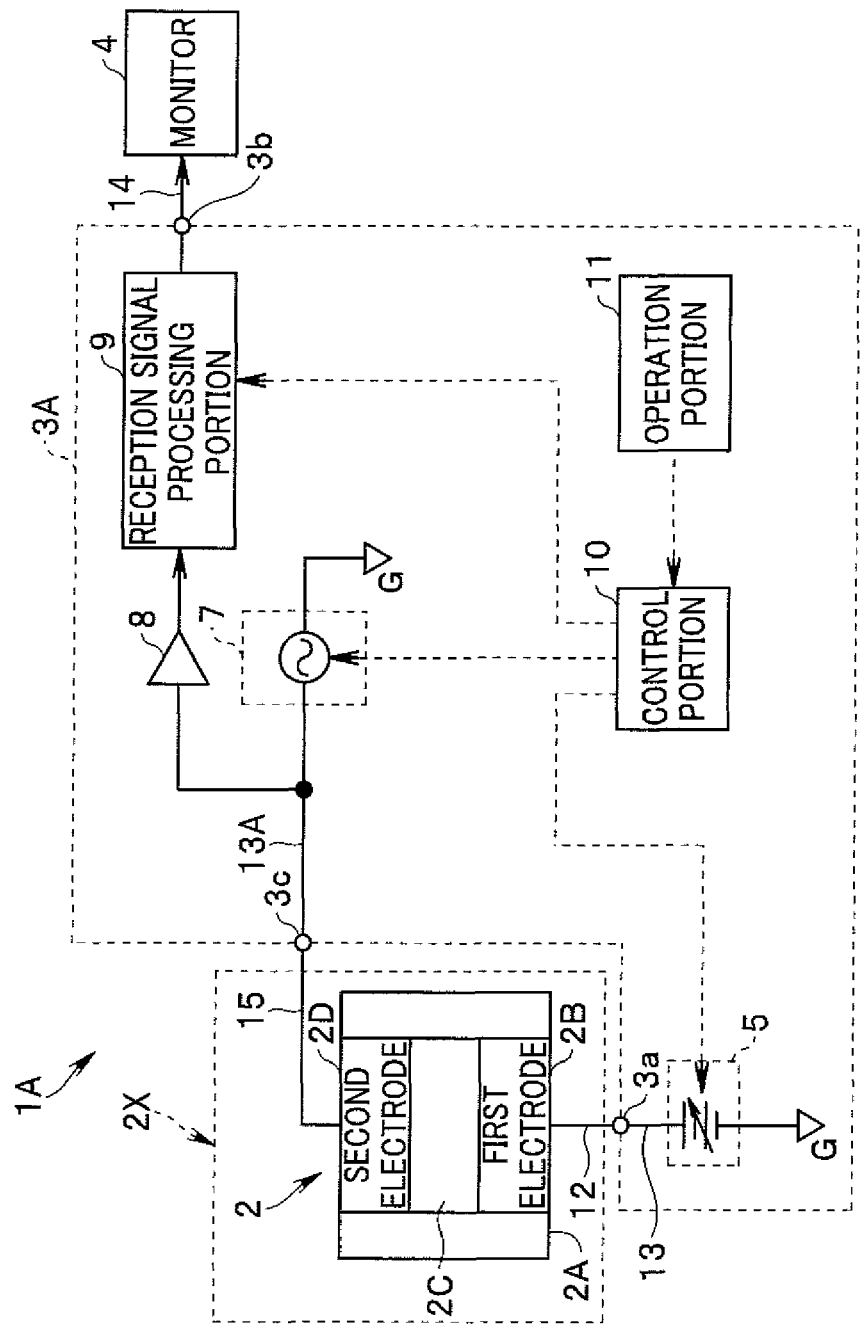
FIG. 5 is a block diagram that shows the overall configuration of an ultrasound diagnostic apparatus according to a second embodiment of the present invention.

FIG. 5 is a block diagram that shows the overall configuration of an ultrasound diagnostic apparatus according to a second embodiment of the present invention. In this connection, components of the ultrasound diagnostic apparatus shown in FIG. 5 that are the same as those of the ultrasound diagnostic apparatus according to the first embodiment are denoted by the same reference symbols and a description of such components is omitted, and only portions that are different from the first embodiment are described below. The ultrasound diagnostic apparatus 1 of the first embodiment is configured so as to apply a bias voltage and a transmission signal to one of the electrodes of the c-MUT element 2, namely, the first electrode 2B. However, an ultrasound diagnostic apparatus 1A of the second embodiment is configured so as to supply a bias voltage to the first electrode 2B of the c-MUT element 2 and supply a transmission signal to the second electrode 2D. That is, the present invention can be applied in the same manner as in the first embodiment even when an electrode to which a bias voltage is supplied and an electrode to which a transmission signal is supplied in the c-MUT element 2 are different.

The specific configuration is shown in FIG. 5.

Although the ultrasound diagnostic apparatus 1A of the present embodiment shown in FIG. 5 has the same components as those of the first embodiment, namely, the ultrasound probe 2X that has the c-MUT element 2, an ultrasound observation apparatus 3A, and the monitor 4, a connection configuration between the c-MUT element 2 of the ultrasound probe 2X and the ultrasound observation apparatus 3A, and the internal configuration of the ultrasound observation apparatus 3A are different from the first embodiment.

More specifically, as shown in FIG. 5, a bias voltage from the ultrasound observation apparatus 3A is applied to the first electrode 2B of the c-MUT element 2, and a transmission signal is applied to the second electrode 2D.

That is, the first electrode 2B is connected to the connection terminal 3a of the ultrasound observation apparatus 3A by the signal wire 12. Further, the second electrode 2D is connected to a connection terminal 3c of the ultrasound observation apparatus 3A by a signal wire 15 that is newly provided.

Although the ultrasound observation apparatus 3A has the same components as those of the first embodiment, the ultrasound observation apparatus 3A includes the newly provided connection terminal 3c as described above.

Inside the ultrasound observation apparatus 3A, the connection terminal 3a is connected to the DC bias output portion 5 via the signal wire 13. Further, the connection terminal 3c is connected to the reception signal processing portion 9 and the transmission signal output portion 7 via a signal wire 13A and the reception signal amplifier 8.

The DC bias output portion 5 generates a bias voltage that is required to drive the c-MUT element 2, and outputs the generated bias voltage to the first electrode 2B of the c-MUT element 2 via the signal wire 13, the connection terminal 3a, and the signal wire 12.

Further, the transmission signal output portion 7 generates an RF signal, that is, a transmission signal as a driving signal, that is required to drive the c-MUT element 2, and outputs the generated transmission signal to the second electrode 2D of the c-MUT element 2 via the signal wire 13A, the connection terminal 3c, and the signal wire 15.

According to this configuration, a transmission signal is applied to the second electrode 2D in a state in which a bias voltage is applied from the first electrode 2B side of the c-MUT element 2. An obtained echo signal (reception signal) is amplified by the reception signal amplifier 8 and inputted to the reception signal processing portion 9.

The reception signal processing portion 9 generates ultrasound image data by subjecting the inputted reception signal to signal processing, and outputs the generated ultrasound image data to the output terminal 3b. The monitor 4 is connected via the signal wire 14 to the output terminal 3b. The ultrasound image data that has been outputted to the output terminal 3b is displayed by the monitor 4.

According to the ultrasound diagnostic apparatus 1A of the present embodiment also, the output timings of a bias voltage and a transmission signal that are applied to the c-MUT element 2 are controlled by the control portion 10.

Similarly to the first embodiment, the operation portion 11 is connected to the control portion 10. The control portion 10 controls the DC bias output portion 5, the transmission signal output portion 7, and the reception signal processing portion 9 based on instruction signals supplied from the operation portion 11.

Further, similarly to the first embodiment, the control portion 10 controls a timing of applying a bias voltage and of transmitting a transmission signal to the c-MUT element 2, and also controls a timing of processing a reception signal obtained by the c-MUT element 2.

That is, according to the present embodiment also, the timing of applying a bias voltage and transmitting a transmission signal to the c-MUT element 2 are controlled by the control portion 10, similarly to the first embodiment.

Figure 6:
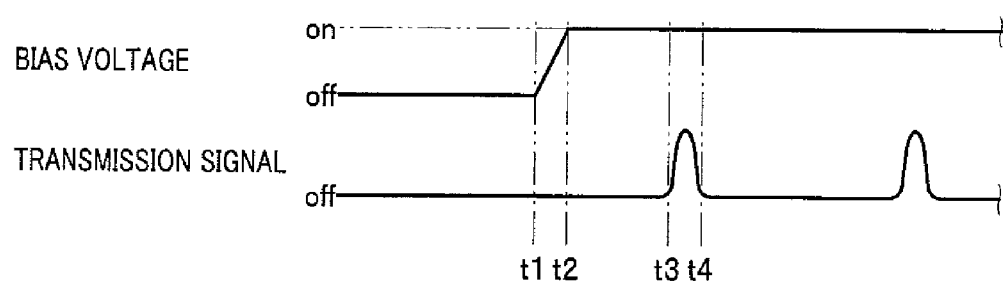
FIG. 6 is a time chart that illustrates changes in a bias voltage and a transmission signal from a time of turning on the power supply of the ultrasound diagnostic apparatus according to the second embodiment.

Changes in the bias voltage and the transmission signal from a time that the power supply is turned on in FIG. 5 are illustrated in FIG. 6. A waveform of the signal wire 12 for supplying a bias voltage that is supplied to the first electrode 2B of the c-MUT element 2 is illustrated by a bias voltage in FIG. 6, while a waveform of the signal wire 15 for supplying transmission and reception signals that are supplied to the second electrode 2D of the c-MUT element 2 is illustrated by a transmission signal in FIG. 6. When it is determined in step S1 of FIG. 2 that the freeze mode has been released by means of the operation portion 11, and it is confirmed in step S2 that the c-MUT element 2 is connected, in step S3 the control portion 10 turns on the DC bias output portion 5. As shown by the bias voltage in FIG. 6, a predetermined bias voltage that has been set in advance is outputted from the time t1 to the time t2. Subsequently, when the transmission signal is outputted in step S4 in FIG. 2, as shown by the transmission signal in FIG. 6, the transmission signal is outputted so as to rise at the time t3 and fall at the time t4.

Figure 7:
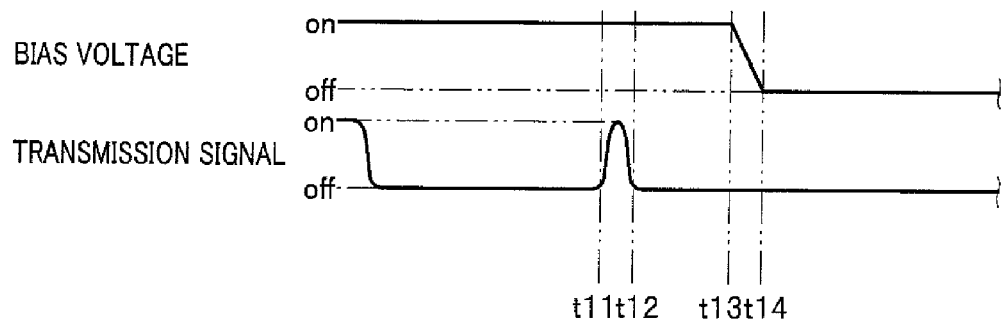
FIG. 7 is a time chart that illustrates changes in a bias voltage and a transmission signal when there is a freeze request according to the ultrasound diagnostic apparatus of the second embodiment.

In contrast, changes in the bias voltage and the transmission signal when there is a freeze request are shown in FIG. 7. When the transmission signal is stopped in step S6 of FIG. 2, as shown by the transmission signal in FIG. 7, the transmission signal is no longer outputted from the time t12 onwards. Further, as shown by the bias voltage in FIG. 7, when the bias output is stopped in step S7 of FIG. 2, output of the bias voltage is stopped in a manner such that the bias voltage is decreased during a period from the time t13 to the time t14 and is zero at the time t14.

The remaining configuration and operations are the same as those of the first embodiment.

Therefore, according to the present embodiment, even when a configuration is adopted so as to supply a bias voltage to the first electrode 2B and supply a transmission signal to the second electrode 2D of the c-MUT element 2, similarly to the first embodiment, since a transmission signal is not transmitted in a state in which a bias voltage is not applied to the c-MUT element 2, damage of the c-MUT element 2 can be prevented.

Third Embodiment

Figure 8:
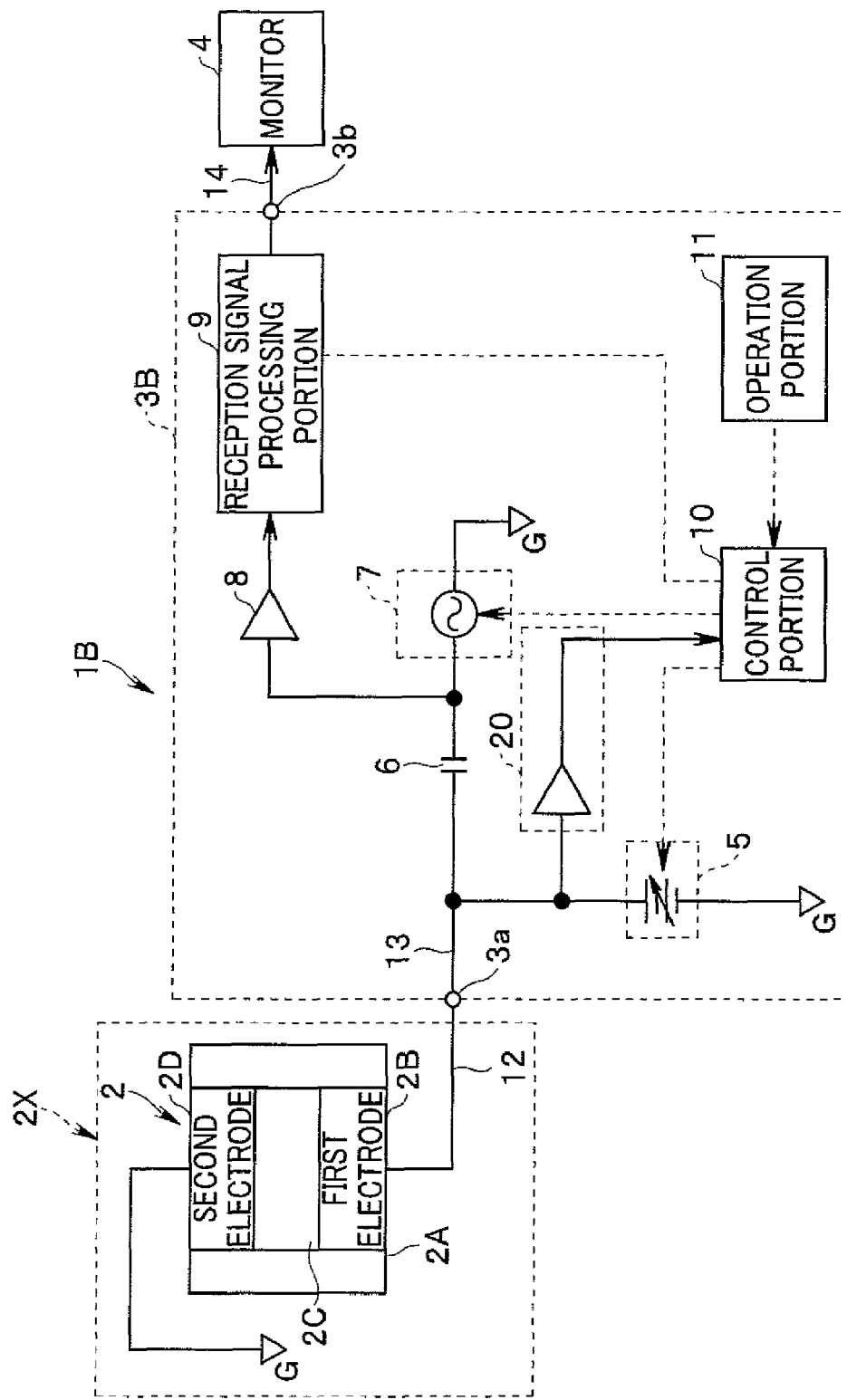
FIG. 8 is a block diagram that shows the overall configuration of an ultrasound diagnostic apparatus according to a third embodiment of the present invention.
Figure 9:
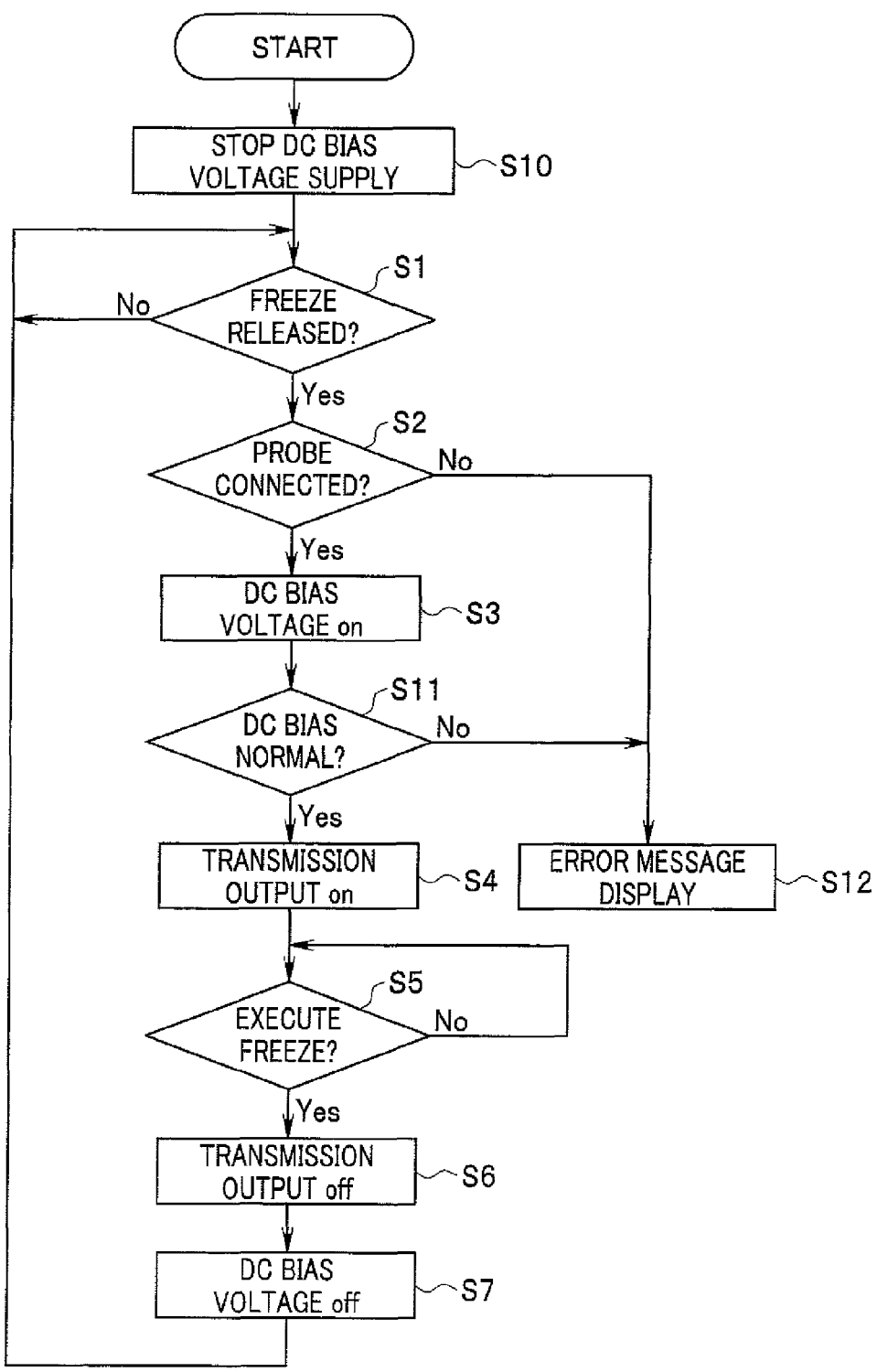
FIG. 9 is a flowchart that illustrates an example of control of a control portion shown in FIG. 8.

FIG. 8 and FIG. 9 relate to a third embodiment of the present invention. FIG. 8 is a block diagram that shows the overall configuration of an ultrasound diagnostic apparatus according to the third embodiment. FIG. 9 is a flowchart that illustrates an example of control of a control portion shown in FIG. 8. In this connection, in the ultrasound diagnostic apparatus shown in FIG. 8 and the flowchart shown in FIG. 9, components and processes that are the same as those of the ultrasound diagnostic apparatus according to the first embodiment are denoted by the same reference symbols and step numbers and a description thereof is omitted, and only portions that are different from the first embodiment are described below.

According to the ultrasound diagnostic apparatuses 1 and 1A of the first and second embodiments, irrespective of the operational status of the c-MUT element 2 that is the supply destination, a bias voltage is applied. Therefore, depending on the situation, there is a possibility that the side of the circuits of the ultrasound observation apparatuses 3 and 3A will be subjected to a load.

Therefore, an ultrasound diagnostic apparatus 1B of the present embodiment is provided with a bias voltage detection portion 20 for monitoring a bias voltage applied to the c-MUT element 2 in order to prevent a load from being applied on the side of the circuit of ultrasound observation apparatus 3B.

The specific configuration is shown in FIG. 8.

Although the ultrasound diagnostic apparatus 1B of the present embodiment shown in FIG. 8 has the same components as the first embodiment, namely, the ultrasound probe 2X that has the c-MUT element 2, an ultrasound observation apparatus 3B, and the monitor 4, the bias voltage detection portion 20 is provided inside the ultrasound observation apparatus 3B.

The configuration other than the bias voltage detection portion 20 is the same as that of the first embodiment. That is, the c-MUT element 2 and the ultrasound observation apparatus 3B are configured and connected in the same manner as in the first embodiment.

According to the present embodiment, as shown in FIG. 8, an input end of the bias voltage detection portion 20 is connected to an output end of the DC bias output portion 5, and an output end of the bias voltage detection portion 20 is connected to the control portion 10.

The bias voltage detection portion 20 detects a bias voltage value that is an output of the DC bias output portion 5, and outputs the detected bias voltage value to the control portion 10.

Also, in the ultrasound diagnostic apparatus 1B of the present embodiment, output timings of a bias voltage and a transmission signal that are applied to the c-MUT element 2 are controlled by the control portion 10 so as to be the same timings as in the first embodiment.

Further, although not shown in the drawings, the control portion 10 has an internal memory. A DC bias voltage specified value (threshold value) that is previously set is stored in the memory. The DC bias voltage specified value is a favorable voltage value for normal operation of the c-MUT element 2. Naturally, the DC bias voltage specified value can be freely set and changed according to the kind of c-MUT element 2 that is used.

In the present embodiment, during a period in which a DC bias voltage is being applied to the c-MUT element 2, the control portion 10 compares a detection result from the bias voltage detection portion 20 and the bias voltage specified value for normally operating the c-MUT element 2. If the detection result from the bias voltage detection portion 20 exceeds the bias voltage specified value, the control portion 10 controls so as to display an error message or the like to that effect on the monitor 4.

It is thus possible to monitor whether a normal DC bias voltage is being outputted to the c-MUT element 2.

Next, operations of the ultrasound diagnostic apparatus according to the present embodiment are described using FIG. 9.

A flowchart that illustrates a specific example of control of the control portion 10 from a time of activating the apparatus according to the present embodiment is shown in FIG. 9.

Here, it is assumed that the power supply is turned on by switching on an unshown power switch to carry out diagnosis and examination of a subject using the ultrasound diagnostic apparatus 1B of the present embodiment.

After the power supply is turned on, the control portion 10 of the ultrasound diagnostic apparatus 1B reads out a program for performing the processing shown in FIG. 9 from an unshown memory and executes the program, and simultaneously performs control to execute the freeze mode.

At this time, since the freeze mode is executed after the power supply is turned on, the ultrasound observation apparatus 3B enters a state in which a bias voltage from the DC bias output portion 5 is not supplied to the c-MUT element 2. That is, when the power supply of the ultrasound diagnostic apparatus 1B is turned on, by the processing in step S10, the control portion 10 controls the DC bias output portion 5 so as not to apply a bias voltage to the c-MUT element 2.

Subsequently, similarly to the first embodiment, in the determination processing in step S1, based on an instruction signal supplied from the operation portion 11, the control portion 10 determines whether or not the freeze mode has been released by an operation of the freeze release key of the operation portion 11 (alternatively, the freeze mode may be released by an operation of the freeze key).

If an instruction to release the freeze mode has been inputted by an operation of the operation portion 11, next, in step S2, the control portion 10 confirms that the c-MUT element 2 is connected. Thereafter, in the processing in step S3, the control portion 10 controls the DC bias output portion 5 so as to output a bias voltage to the c-MUT element 2. The processing then shifts to execute determination processing in step S11.

If the result determined by the determination processing in the above described step S2 is that the c-MUT element 2 is not connected, next, the control portion 10 performs the processing in step S12 to display a message to the effect that the c-MUT element 2 is not connected on the screen of the monitor 4, and thereafter returns the processing to the above described step S1.

Note that a piezoelectric ultrasound transducer that is other than the c-MUT element 2 can also be connected to the ultrasound diagnostic apparatus of the present embodiment. Therefore, a configuration may also be adopted in which, in the processing of the above described step S2, the control portion 10 detects which one of the c-MUT element 2 and a piezoelectric ultrasound transducer is connected, and in the processing of the above described step S12, a connection state showing which ultrasound transducer is connected is displayed on the screen of the monitor 4.

In the determination processing in step S11, the control portion 10 compares a detection result from the bias voltage detection portion 20 and the bias voltage specified value for normally operating the ultrasound diagnostic apparatus, and determines whether or not the detection result from the bias voltage detection portion 20 is normal.

In this case, if the detection result from the bias voltage detection portion 20 is the same as or less than the bias voltage specified value, the control portion 10 determines that the detection result is normal. Conversely, if the detection result exceeds the bias voltage specified value, the control portion 10 determines that the detection result is not normal.

If it is determined in this case that the detection result from the bias voltage detection portion 20 is not normal, in the processing in step S12, the control portion 10 controls so as to display an error message or the like that shows that the DC bias voltage is greater than the bias voltage specified value and is not a normal value on the screen of the monitor 4, and thereafter returns the processing to step S1.

In contrast, if it is determined that the detection result from the bias voltage detection portion 20 is normal, next, in the processing in step S4, the control portion 10 controls the transmission signal output portion 7 so as to output a transmission signal.

While continuing output of the transmission signal in the processing in step S4, the control portion 10 carries out determination processing by executing the subsequent step S5. In the determination processing in step S5, based on an instruction signal supplied from the operation portion 11, the control portion 10 determines whether or not a request has been made to execute the freeze mode by operation of the freeze key of the operation portion 11.

If an instruction has been inputted to request execution of the freeze mode by operation of the operation portion 11, in the subsequent step S6, the control portion 10 controls the transmission signal output portion 7 so as to stop output of the transmission signal. Thereafter, in the processing in step S7, the control portion 10 controls the DC bias output portion 5 so as to stop output of the bias voltage that is being outputted to the c-MUT element 2.

In this connection, the output timings of the bias voltage and the transmission signals that are applied to the c-MUT element 2 are controlled in the same manner as in the first embodiment.

Thus, the control portion 10 executes the freeze mode, and thereafter returns the processing to step S1 to continue the determination processing in step S1.

Note that, although not shown in the flowchart in FIG. 9, the DC bias voltage detection portion 20 may also be actuated during a period in which ultrasound is being generated by the c-MUT element 2 (during scanning), in addition to a period in which a bias voltage is being applied to the c-MUT element 2. As a result, if the DC bias voltage exceeds the bias voltage specified value or is a value that is different to a set value, an error message may be displayed on the screen of the monitor 4 and the freeze mode may be executed in the same manner as a time of a freeze mode request, by performing control procedures so as to stop output of a transmission signal and thereafter decrease and stop the DC bias voltage.

Further, although the control portion 10 executes control to display an error message or the like on the screen of the monitor 4 based on the result of comparing the detection result from the DC bias voltage detection portion 20 with the bias voltage specified value, the present invention is not limited thereto.

For example, the control portion 10 may control so as to continuously display an output state of a bias voltage generated by the DC bias output portion 5 on the screen of the monitor 4 based on a detection result from the DC bias voltage detection portion 20, to thereby enable monitoring of the bias voltage that is applied to the c-MUT element 2.

Thus, according to the present embodiment, in addition to obtaining the same effects as those of the first embodiment, by adopting a configuration in which the bias voltage detection portion 20 is provided for monitoring the bias voltage that is applied to the c-MUT element 2, it is possible to prevent the side of the ultrasound observation apparatus 3B circuit from being subjected to a load due to application of a bias voltage.

The present invention is not limited to the embodiments and modification examples described above, and various changes and modifications are possible within a range that does not depart from the scope of the present invention.

What is claimed is:

1. An ultrasound diagnostic apparatus that is connectable with an ultrasound probe having a capacitive micro-machined ultrasonic transducer whose sensitivity can be controlled in accordance with an applied bias voltage, comprising:
   a bias voltage output portion capable of varying the bias voltage that is applied to the capacitive micro-machined ultrasonic transducer;
   a transmission signal output portion that outputs an ultrasound transmission signal to the capacitive micro-machined ultrasonic transducer;

an operation portion that outputs an instruction signal that instructs the ultrasound diagnostic apparatus including the bias voltage output portion and the transmission signal output portion; and a control portion that, based on an instruction signal from the operation portion, controls the bias voltage output portion and the transmission signal output portion to control output timings of the bias voltage and the transmission signal so as to output the ultrasound signal after outputting the bias voltage or to stop output of the bias voltage after stopping output of the ultrasound signal;

wherein:

a piezoelectric ultrasound transducer that does not require bias voltage control can be connected to the ultrasound diagnostic apparatus, and the ultrasound diagnostic apparatus further includes a display portion that displays an ultrasound image based on a reception signal that is received by the capacitive micro-machined ultrasonic transducer; and the control portion causes a connection state that shows which one of the piezoelectric ultrasound transducer and the capacitive micro-machined ultrasonic transducer is connected to be displayed on the display portion.

2. The ultrasound diagnostic apparatus according to claim 1, wherein: the operation portion outputs at least instruction signals that instruct a start of transmission and stopping of transmission of the ultrasound transmission signal by the transmission signal output portion; and when an instruction signal that instructs a start of transmission is inputted from the operation portion, the control portion controls the bias voltage output portion and the transmission signal output portion so as to output the bias voltage and thereafter output the ultrasound transmission signal, and when an instruction signal that instructs stopping of transmission is inputted from the operation portion, the control portion controls the bias voltage output portion and the transmission signal output portion so as to stop output of the ultrasound transmission signal and thereafter stop output of the bias voltage.

3. The ultrasound diagnostic apparatus according to claim 1, wherein:

the control portion controls the bias voltage output portion so as not to apply the bias voltage when a power supply of the ultrasound diagnostic apparatus is turned on.

4. The ultrasound diagnostic apparatus according to claim 1, wherein:

when the capacitive micro-machined ultrasonic transducer is not connected when an instruction signal that instructs a start of transmission is inputted from the operation portion, the control portion controls the bias voltage output portion so as not to apply the bias voltage.

5. The ultrasound diagnostic apparatus according to claim 1, further comprising:

a bias voltage detection portion for monitoring that a bias voltage that is being applied to the capacitive micro-machined ultrasonic transducer is a specified value during a period in which ultrasound is being transmitted from the capacitive micro-machined ultrasonic transducer.

6. The ultrasound diagnostic apparatus according to claim 1, wherein:

the control portion causes an output state of the bias voltage that is outputted by the bias voltage output portion to be displayed on the display portion.

* * * * *